United States Patent [19]
Lennon et al.

[11] Patent Number: 5,859,278
[45] Date of Patent: Jan. 12, 1999

[54] METHOD FOR PREPARING CYANOPHOSPHONATE DERIVATIVES FROM PYROPHOSPHATE OR POLYPHOSPHATE ESTERS AND CYANIDE

[75] Inventors: Patrick J. Lennon, Webster Grove; Sergey G. Vulfson, Chesterfield, both of Mo.

[73] Assignee: Monsanto Company, St. Louis, Mo.

[21] Appl. No.: 996,945

[22] Filed: Dec. 23, 1997

[51] Int. Cl.$^6$ ............... C07F 9/40; C07F 9/38; C01B 25/26; C01B 25/18
[52] U.S. Cl. ............ 558/87; 423/302; 558/145; 558/166; 558/167; 562/16
[58] Field of Search ............ 423/302; 558/87, 558/145, 166, 167; 562/16

[56] References Cited

U.S. PATENT DOCUMENTS

| | | | |
|---|---|---|---|
| 2,402,703 | 6/1946 | Woodstock . | |
| 2,702,299 | 2/1955 | Harris . | |
| 3,432,277 | 3/1969 | Roesky | 23/357 |
| 3,812,221 | 5/1974 | Braden et al. | 260/968 |
| 4,221,583 | 9/1980 | Gaertner et al. . | |
| 4,568,432 | 2/1986 | Rogers | 204/73 |

FOREIGN PATENT DOCUMENTS

| | | | |
|---|---|---|---|
| 300 936 | 9/1992 | Germany | C07F 9/40 |
| 96/15135 | 5/1996 | WIPO | C07F 9/38 |

OTHER PUBLICATIONS

Abstract–Database WPI, Section Ch, Week 7615, Derwent Publications Ltd., London, GB; Class B04, AN 76–27192X, XP002061354 & JP 51 023 225 A (Nippon Chem. Ind. Co. Ltd.), 24 Feb. 1976.

Blanchard, J. "Préparation d–acides beta–amino–ethyl–phosphoniques" *Tetrahedron*, vol. 32, No. 4, 1976, Oxford GB, pp. 455–459, XP002061374.

Chemical Abstracts, vol. 093, No. 12, 22 Sep. 1980, Columbus, Ohio, US; abstract No. 123612, Zhurba, Y.I. et al. "Increase in the stability of silver complexes in the process of simultaneous developing and fixing" and ZH Nauchn, Pirkl. Fotogr. Kinematogr. (Znpfag, 00444561); 80; vol. 25(3); pp. 182–5, Vses. Gos. Nauchno–Issled. Proektn. Inst. Khim.–Fotogr. Prom., Moscow; USSR; XP002061352.

Dyatkina, N. et al. Synthesis and antiviral activity of some fluorinated nucleotide derivativers: Nucleosides Nucleotides (Nunud5, 07328311); 94; col. 13 (1–3); pp. 325–337, Engelhardt Inst. Mol. Biol.; Mowcow; 117984, Russia XP002061348.

Kashemirov, B.A. "(E)–(Hydroxyimino)(hydroxymethoxyphosphinyl)acetic acid: Synthesis and pH dependent fragmentation," *Tetrahedron Letters*, vol. 36, No. 52, 1995, Oxford GB, pp. 9437–9440; XP002061351.

Albrecht et al., "Reaction of the Two–Component System Trialkyl Phosphite/Carbon Tetrachloride with Nucleophiles 3. Reaction in Presence of Trialkylammonium Salts," *Z. anorg. allg. Chem.* 552: 132–146 (1987) and English language translation.

Kashemirov et al., "Troika Acids: Synthesis, Structure, and Fragmentation Pathways of Novel α–(Hydroxyimino)phosphonacetic Acids," *J. Am. Chem. Soc.* 117: 7285–7286 (1995).

Shioiri et al., "Reaction of Diethyl Phosphorocyanidate)DEPC) with Carboxylic Acids. A New Synthesis of Carboxylic Esters and Amides," *Tetrahedron* 32(18): 2211–2217 (1976).

Tung et al., "A New Method for the Preparation of O,O'–Dialkylphosphoryl Cyanides," *Hua Hsueh Hsueh Pao (Acta Chimica Sinica)* 31(3): 199–202 (1965).

*Primary Examiner*—Michael G. Ambrose
*Attorney, Agent, or Firm*—James M. Warner; Arnold, White & Durkee

[57] ABSTRACT

A process for preparing cyanophosphonate derivatives involves contacting a pyrophosphate ester or a polyphosphate ester and cyanide in a reaction mixture under conditions sufficient to produce the cyanophosphonate derivative. The cyanophosphonate derivative product can subsequently be hydrogenated to produce an aminomethylphosphonate derivative.

47 Claims, No Drawings

METHOD FOR PREPARING CYANOPHOSPHONATE DERIVATIVES FROM PYROPHOSPHATE OR POLYPHOSPHATE ESTERS AND CYANIDE

This application claims the benefit of provisional application Ser. No. 60/034,521, filed Dec. 30, 1996.

BACKGROUND OF THE INVENTION

Phosphorus-containing compounds such as cyanophosphonate derivatives are important precursors for the synthesis of organophosphorus compounds, which have numerous applications, for example, in herbicides, insecticides, fertilizers, flame retardants and plasticizers. Cyanophosphonate derivatives can be further converted to aminomethylphosphonate derivatives, which have been particularly important precursors in the synthesis of N-phosphonomethylglycine, a highly effective commercial herbicide (available under the trade name Roundup™) useful for the control of a large variety of weeds. The syntheses of such organophosphorus compounds have commonly used a halogen derivative of phosphorus as a starting material.

There is a need in the art for alternative processes for preparing cyanophosphonate derivatives and novel cyanophosphonate derivatives to be used in the synthesis of other phosphorus species. There is a further need for such novel processes and compounds that are economical and have an improved environmental impact over conventional processes using halogen-containing starting materials.

SUMMARY OF THE INVENTION

This invention relates to a process for preparing cyanophosphonate derivatives. More particularly, the invention is directed to a process that involves contacting a pyrophosphate ester or a polyphosphate ester and a cyanide in a reaction mixture under sufficient conditions to produce a cyanophosphonate derivative. That cyanophosphonate derivative can be subsequently hydrogenated to produce an aminomethylphosphonate derivative. In a preferred embodiment, the cyanophosphonate derivative and the aminomethylphosphonate derivative are used as precursors for the production of N-phosphonomethylglycine.

The process according to the invention offer significant advantages in that it provide a novel, economical route to synthesize cyanophosphonate derivatives having an improved environmental impact over conventional processes using halogen-containing starting materials.

DESCRIPTION OF ILLUSTRATIVE EMBODIMENTS

The invention is broadly directed to a process that involves contacting a pyrophosphate ester or a polyphosphate ester and a cyanide in a reaction mixture under sufficient conditions to produce a cyanophosphonate derivative. That cyanophosphonate derivative can be subsequently hydrogenated to produce an aminomethylphosphonate derivative. In a preferred embodiment, the cyanophosphonate and aminomethylphosphonate derivatives produced by the inventive process are precursors for the production of N-phosphonomethylglycine.

The phosphate reagent for the cyanophosphonate derivative synthesis according to the invention is generally selected from pyrophosphate esters (I) and polyphosphate esters (II):

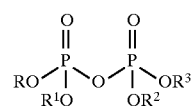

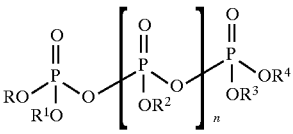

wherein R, $R^1$, $R^2$, $R^3$ and $R^4$ can be the same or different and are defined as an aryl group, an arylalkyl group or a straight or branched alkyl group having from 1 to 20 carbon atoms, and more preferably 1 to 10 carbon atoms, and n is an integer, preferably from 0 to 10, more preferably from 0 to 5 and most preferably from 1 to 3. The alkyl group most preferably has 1 to 4 carbon atoms and the arylalkyl group is most preferably a benzyl group.

The pyrophosphate ester is preferably a tetraalkyl, tetraaryl, or a tetra(arylalkyl) pyrophosphate of the formula (I), wherein R, $R^1$, $R^2$ and $R^3$ can be the same or different, and preferably are the same. In a further preferred embodiment, the pyrophosphate ester is tetrabenzylpyrophosphate or tetraethylpyrophosphate. The polyphosphate ester is preferably of the formula (II), wherein R, $R^1$, $R^2$, $R^3$ and $R^4$ are the same or different, and are preferably the same. Where n is greater than 1, the multiple substituents represented by $R^2$ can also be the same or different. In a further preferred embodiment, the polyphosphate ester is hexaethyltetraphosphate (preparation disclosed in U.S. Pat. No. 2,402,703, which is incorporated herein by reference).

The cyanide reagent can be hydrogen cyanide or a cyanide salt that is sufficiently reactive with a pyrophosphate or polyphosphate ester to produce a cyanophosphonate derivative. For example, the cyanide compound can be an alkali metal cyanide, an alkaline earth metal cyanide, an ammonium cyanide, a tetraalkyl ammonium cyanide, a tetraalkyl phosphonium cyanide, a tetraaryl phosphonium cyanide, a trialkyl sulfonium cyanide, a cyanide of a cationic form of an organic amine or mixtures thereof. The cyanide compound is preferably hydrogen cyanide, potassium cyanide, sodium cyanide, lithium cyanide, silver cyanide, gold cyanide, copper cyanide, tetrabutylammonium cyanide or mixtures thereof. More preferably, the cyanide reagent is hydrogen cyanide, potassium cyanide, sodium cyanide or tetrabutylammonium cyanide. The cyanide is added to the reaction mixture in an amount such that the molar ratio of cyanide ion to phosphorus atoms (i e., one phosphorus atom per phosphate group, two phosphorus atoms per pyrophosphate ester, etc.) added to the reaction mixture is about 0.9 to about 10, more preferably in the range of about 1 to about 4 and most preferably in the range of about 1.5 to about 2.5 or in the range of 0.9 to 1.2.

In a preferred embodiment, the cyanophosphonate derivative synthesis reaction mixture further contains a solvent. The solvent can be any compound suitable for enhancing the solubility of the reactants or providing a medium for the reaction, and is preferably a polar, aprotic solvent. For example, the solvent is preferably an amide, a nitrile or an ether, for example, N,N-dimethylformamide (DMF), dimethylacetamide, acetonitrile, propionitrile, tetrahydrofuran or methyl t-butyl ether.

The conditions of the inventive process are those conditions sufficient to promote the formation of the desired cyanophosphonate derivative product in the reaction mixture. The reaction temperature is preferably in the range of about 0° to about 100° C., more preferably in the range of about 20 to about 80° C. and most preferably in the range of about 30° to about 60° C. The reaction is generally conducted with moderate stirring of the reaction mixture. The reaction time can range from about 0.5 to about 15 hours, preferably from about 1 to about 5 hours and most preferably from about 1.5 to about 4 hours.

The cyanophosphonate derivative product, if necessary, is preferably precipitated from the reaction mixture by conventional methods that promote precipitation. For example, the solvent originally added to the reaction mixture can be removed by vacuum pump, and a material such as toluene can be added to the reaction mixture to promote precipitation of the cyanophosphonate derivative product. That composition can then be stirred or settled for a period of time until substantially all of the cyanophosphonate product is precipitated. The resulting precipitate can be further purified, for example, by filtration and/or washing with a solvent such as acetone.

The cyanophosphonate derivative product from the inventive step of contacting the pyrophosphate or polyphosphate ester and cyanide can directly or indirectly be a cyanophosphate disalt, a cyanophosphonate monosalt monoester, a cyanophosphonate diester, a cyanophosphonate monosalt monoacid, a cyanophosphonate monoacid monoester or cyanophosphonic acid. When the phosphate reagent is a pyrophosphate ester, the cyanophosphonate derivative produced is generally a monosalt monoester of cyanophosphonate. For example, the cyanophosphonate derivative produced by the inventive process can be potassium benzyl cyanophosphonate, potassium methyl cyanophosphonate, potassium ethyl cyanophosphonate, lithium benzyl cyanophosphonate, lithium methyl cyanophosphonate, lithium ethyl cyanophosphonate, sodium benzyl cyanophosphonate, sodium methyl cyanophosphonate or sodium ethyl cyanophosphonate. The benzyl esters of cyanophosphonate can be further hydrogenated to produce cyanophosphonate mono- or disalts. The cyanophosphonate derivative product is preferably produced in at least 30% yield with respect to the phosphate reagent, more preferably at a 40–90% yield and most preferably at a 50–80% yield, wherein the yield is defined as the [cyanophosphonate derivative product]/[phosphate ester reagent], with the understanding that the yield can be greater than 100% in processes using polyphosphates.

The cyanophosphonate derivative produced by the inventive process can be used as a precursor for producing other organophosphorus species. In a preferred embodiment, the cyanophosphonate derivative product can be hydrogenated to produce an aminomethylphosphonate derivative. The hydrogenation can take place by contacting the cyanophosphonate derivative with hydrogen in the presence of a suitable catalyst under sufficient conditions to produce an aminomethylphosphonate derivative. The cyanophosphonate derivative can be provided alone or in a mixture of compounds, including a product mixture or portion of a product mixture from the reaction of a phosphate ester and cyanide.

Preferably, the hydrogenation further involves the presence of a solvent. The solvent can be any material that enhances the solubility of reactants or promotes the formation of the desired products. In a preferred embodiment, the solvent is water, acetic acid, an alcohol, dimethylacetamide, an anhydride, e.g., acetic anhydride, an amide, sulfolane or mixtures thereof.

Hydrogen pressure can be maintained at a level suitable for the formation of an aminomethylphosphonate derivative, and consistent with safety limitations of the experimental system. In a preferred embodiment, the hydrogen pressure is between about 0.25 and 5000 psi, more preferably between about 0.5 and about 3000 psi and most preferably between about 1 and about 1000 psi, for example, between about 25 and about 300 psi.

In a preferred embodiment, the catalyst is a transition metal catalyst. For example, the hydrogenation step can use a catalyst of a cobalt-containing compound, a nickel-containing compound, a platinum-containing compound, a palladium-containing compound or a rhodium-containing compound. More preferably, the catalyst is Raney cobalt, Raney nickel, platinum tetrachloride ($PtCl_4$) promoted Raney nickel, platinum on carbon, palladium on carbon or rhodium on carbon. The catalyst can be used at a stoichiometric amount or catalytic amount with respect to the cyanophosphonate derivative. The stoichiometric amount is preferably between about 1 molar equivalent and 5 molar equivalents with respect to the cyanophosphonate derivative, and more preferably between about 1 molar equivalent and 2 molar equivalents with respect to the cyanophosphonate derivative. The catalytic amount is preferably between about 0.1 molar percent and 100 molar percent with respect to the cyanophosphonate derivative, and more preferably between about 0.5 molar percent and 50 molar percent with respect to the cyanophosphonate derivative.

In the event that a catalyst of platinum on carbon, palladium on carbon or rhodium on carbon is used, the hydrogenation reaction mixture preferably further contains an acid in an amount sufficient to promote formation of the desired product. The acid can be an inorganic acid or an organic acid. The inorganic acid is preferably hydrochloric acid, sulfuric acid, phosphoric acid, nitric acid or hydrocyanic acid and, more preferably, hydrochloric acid. The organic acid is preferably acetic acid, trifluoroacetic acid, trifluoromethanesulfonic acid or p-toluenesulfonic acid. The acid can be added to the hydrogenation reaction mixture at a concentration between about 0.1 and 5 molar equivalents with respect to the cyanophosphonate derivative, more preferably at a concentration between about 0.5 and 2.5 molar equivalents with respect to the cyanophosphonate derivative, and most preferably at a concentration of about 1 molar equivalent or about 2 molar equivalents with respect to the cyanophosphonate derivative, depending on the degree of protonation.

In a preferred embodiment, the reaction product mixture from the hydrogenation step is heated under sufficient conditions to further promote the formation of the aminomethylphosphonate derivative. For example, a product mixture that has been partially or substantially hydrogenated can be heated to a temperature in the range of about 135° C. to about 200° C., and more preferably to a range of about 135° C. to about 160° C. This heating step may be conducted for any amount of time that further promotes the aminomethylphosphonate derivative formation, preferably about 1 to about 12 hours. The heating time for optimum aminomethylphosphonate derivative formation can depend on the pH and the nature of the cations in the reaction mixture.

The products of the hydrogenation step can be isolated from the reaction mixture by conventional methods or can be used for some purposes without isolation from the reaction product mixture. Further details regarding cyanophosphonate derivative hydrogenation are provided in co-pending U.S. application Ser. No. 08/996,948 entitled "Method for Preparing Aminomethylphosphonate Derivatives Via Hydrogenation of Cyanophosphonate Derivatives," by Patrick J. Lennon, filed Dec. 23, 1997 which is incorporated herein by reference.

The aminomethylphosphonate derivative product of the inventive process can be used as a precursor for producing other organophosphorus species. In a preferred embodiment, aminomethylphosphonic acid is used for producing N-phosphono-methylglycine. Methods for producing N-phosphonomethylglycine from aminomethylphosphonic acid are disclosed, for example, in U.S. Pat. No. 4,221,583 (Monsanto Co.), which is incorporated herein by reference.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Reaction of Tetrabenzylpyrophosphate with Cyanide

Tetrabenzylpyrophosphate (0.89 g, 1.65 mmol) was mixed with 5 ml of dry DMF, after which KCN (0.20 g, 3.13 mmol) was added. The reaction mixture was stirred for 2 hours at 40° C., after which the $^{31}$P NMR spectrum showed that no starting material remained. There were three signals at about −0.5 ppm (quintet, 36%), −1.5 ppm (septet, 18%), and −21.5 ppm (triplet, 46%). After removing the DMF (vacuum pump), toluene (15 ml) was added to the reaction mixture and stirred overnight. A precipitate was formed which was filtered, then washed twice with dry acetone (100 ml, 0.32 g).

The product gave NMR spectra consistent with that of (BzO)$_2$(KO)PO, as well as a molecular ion in negative ion FAB mass spectrum. The toluene solution was evaporated to obtain an oil (0.08 g), which was washed with acetone (5 ml). Although the $^{31}$P NMR of this oil contained only one signal at −1.5 ppm, the GS-MS spectral analysis showed the presence of two molecular species: (OBz)$_3$PO (M+368, CI) and PhCH$_2$CN (M+117). The identities of the dibenzyl- and tribenzylphosphate products were confirmed by the addition of authentic neutral materials and repeating the $^{31}$P NMR spectra. The acetone fractions were combined and ether (500 ml) was added, precipitating a white solid (0.21 g). The NMR spectra were consistent with this product being (BzO)(KO)P(O)CN; a molecular ion for (PhCH$_2$O)(O)P(CN)O was observed in the negative ion FAB mass spectrum at m/e 196.

This product was hydrogenolyzed in methanol under hydrogen using Pd/C as catalyst, giving (HO)(KO)P(O)CN. This solution was treated with one equivalent of KOH to give (KO)$_2$P(O)CN having spectra identical with independently prepared material.

Example 2

Reaction of Tetraethylpyrophosphate with Cyanide

Tetraethylpyrophosphate (0.20 g, 0.69 mmol) was dissolved in dry DMF (2 ml), after which K$^{13}$CN (0.096 g, 1.45 mmol) was added. The reaction mixture was heated at 50° C. overnight. According to $^{31}$P NMR, the crude reaction mixture showed three signals: −21.7 ppm (doublet of triplets, $^1J_{PC}$=154.1 Hz, $^3J_{PH}$=7.6 Hz, 47.5%, consistent with the formulation, (EtO)(KO)P(O)CN); −2 ppm, (septet, $^3J_{PH}$=7.6 Hz, 5.0%, consistent with the formulation, (EtO)$_3$PO); and −1 ppm, (quintet, $^3J_{PH}$=6.1 Hz, 47.5%, formulated as (EtO)$_2$(KO)PO). The solvent was removed under reduced pressure and collected in a trap cooled in dry ice. CI Mass spectroscopy showed the presence of (EtO)$_3$PO and also CH$_3$CH$_2$CN in the DMF fraction.

The mass spectrum of the residue which remained showed molecular ions for the two anions by negative FAB mass spectrometry. Also, the $^{31}$P and $^3$C NMR spectra were recorded for the samples in which the following authentic compounds (EtO)(KO)P(O)CN, (EtO)$_2$(KO)PO, (EtO)$_3$PO, and CH$_3$CH$_2$CN (obtained by alternative synthesis or commercially) were added.

Example 3

Reaction of Hexaethyltetraphosphate with Cyanide

The procedure for preparing hexaethyltetraphosphate, as provided by the disclosure of U.S. Pat. No. 2,402,703, was conducted by slowly adding P$_4$O$_{10}$ (0.94 g, 3.3 mmol) to triethylphosphate (2.4 g, 13.2 mmol) in a flask cooled in a water bath so as to keep the internal temperature at about 50° C. The mixture was stirred for 3 hours at this temperature to give a clear solution which was reported to be predominantly hexaethyltetraphosphate. Although the $^{31}$P NMR was quite complex, it had only minimal amounts of either of the starting materials.

After sitting at room temperature under inert atmosphere for about four days, the reaction mixture was divided into two equal parts which were dissolved in dry acetonitrile (1 ml each) to react overnight with K$^{12}$CN (0.86 g, 13.2 mmol) and K$^{13}$CN (0.87 g, 13.2 mmol) at 50° C.

After 16 hours, the acetonitrile was removed from both reactions under reduced pressure, and D$_2$O (about 1 ml each) was added. $^{31}$P NMR analysis gave a 51% yield of compounds containing P-CN groups. In the reaction with K$^{13}$CN, one signal accounted for 49% of the total $^{31}$P signal at −20 ppm (doublet of triplets, $^1J_{PC}$=164.8 Hz, $^3J_{PH}$=7.6 Hz, (OEt)(OK)P(O)CN), and 2% of the $^{31}$P signal had multiple small P-CN signals with a major peak at −34.5 ppm, (doublet of doublets, $^1J_{PC}$=194.6 Hz, $^3J_{PC}$=17 Hz). For the reaction with K$^{12}$CN, a similar result was observed in the $^{31}$P NMR spectrum (D$_2$O): −19.8 ppm (51%, (OEt)(OK)P(O)CN), −31 to −35 ppm, 0.4% other P-CN containing products).

Example 4

Reaction of Tetrabenzylpyrophosphate with Hydrocyanic Acid

Tetrabenzylpyrophosphate (3.49 g, 6.48 mmol) was mixed with quinuclidine (1.45 g, 13.06 mmol), then dissolved in dry acetonitrile (15 ml), and was cooled in an ice bath, after which liquid HCN (0.5 ml, 12.7 mmol, distilled from 1.7g H$_2$SO$_4$ in 0.7 ml H$_2$O and a mixture of K$^{12}$CN (1.28 g) and K$^{13}$CN (1.0 g) in 4 ml H$_2$O) was added at 0° C. The reaction mixture was stirred for 19 hours at 40° C., then the reaction was stopped and was purged by nitrogen for two hours. The $^{31}$P NMR spectrum showed that no starting material remained. There were three signals in the $^{31}$P NMR spectrum at about −0.8 ppm (quintet, $^3J_{PH}$=6.1 Hz, 34%, probably (BzO)$_2$(O')PO); −12.3 ppm (t, $^3P_{PH}$=3.1 Hz, 33%); and −22.5 ppm (dt, $^1J_{PC}$=154.1 Hz, $^3J_{PH}$=9.1 Hz, 33%), consistent with the formulation as (BzO)(O')(CN)PO. A coupling constant of $^1J_{CP}$=154.6 Hz was found for signal at 120.5 ppm in $^{13}$C NMR spectrum.

Example 5

General Procedure for Low Pressure Hydrogenations

Dipotassium cyanophosphonate (0.133 g, 1.0 mmol) was added to Raney nickel (0.118 g, as a 50% slurry in water, W2 form) in a Fisher Porter bottle containing a stir bar. Water (5 ml) was added, and platinum tetrachloride (0.105 g, 0.31 mmol) was added. The pressure bottle was immediately connected to a hydrogen manifold, and three purges with hydrogen at 75 psi were done, and the bottle was pressurized to 75 psi. The reaction mixture was vigorously stirred for 25.5 hours at room temperature. The pressure was then released and the reaction mixture was filtered. HPLC Analysis determined a 63% yield of aminomethylphosphonic acid.

Example 6

General Procedure for Hydrogenation in Autoclave

In a 300 ml Autoclave Engineers autoclave, Na$_2$O$_3$PCN (H$_2$O)$_{0.49}$ (0.80 g, 5.0 mmol) was added, followed by 10% Pt/C (0.15 g), water (100 ml), and then HCl·dioxane (2.5 ml, 4N, 10.0 ml). The autoclave was sealed, pressured once with nitrogen above 500 psi, vented, and pressured with hydrogen to 1001 psi. Stirring at about 1500 rpm was started. Within about 10 minutes, the internal pressure was about 996 psi, and the autoclave internal temperature was about 26° C. After stirring overnight, the hydrogen was vented, the autoclave was repressurized with nitrogen and vented, and then the reactor was opened and the reaction mixture removed. The reaction mixture was filtered, and the resulting solution analyzed by HPLC. The yield by HPLC of aminomethylphosphonic acid was 85%, and by NMR 87%.

While the compositions and methods of this invention have been described in terms of preferred embodiments, it will be apparent to those of skill in the art that variations can be applied to the process described herein without departing from the concept, spirit and scope of the invention. All such similar substitutes and modifications apparent to those skilled in the art are deemed to be within the spirit, scope and concept of the invention.

What is claimed is:

1. A process for preparing a cyanophosphonate derivative comprising:
   contacting a pyrophosphate ester or a polyphosphate ester and a cyanide in a reaction mixture under sufficient conditions to produce a cyanophosphonate derivative.

2. The process of claim 1, wherein the ester is a pyrophosphate ester of the formula

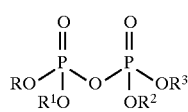

(I)

wherein R, R$^1$, R$^2$ and R$^3$ are the same or different and are defined as an aryl group, an arylalkyl group or a straight or branched alkyl group having from 1 to 20 carbon atoms.

3. The process of claim 2, wherein the aryl, arylalkyl or alkyl groups have from 1 to 10 carbon atoms.

4. The process of claim 3, wherein the alkyl group has from 1 to 4 carbon atoms.

5. The process of claim 2, wherein the arylalkyl group is a benzyl group.

6. The process of claim 2, wherein the ester is a tetraalkyl pyrophosphate, a tetraaryl pyrophosphate or a tetra (arylalkyl)pyrophosphate.

7. The process of claim 6, wherein the ester is tetraethylpyrophosphate.

8. The process of claim 6, wherein the ester is tetrabenzylpyrophosphate.

9. The process of claim 1, wherein the ester is a polyphosphate ester.

10. The process of claim 1, wherein the ester is a polyphosphate ester of the formula

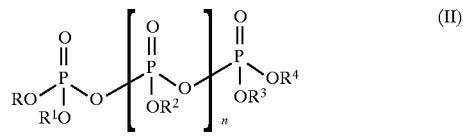

(II)

wherein R, R$^1$, R$^2$, R$^3$ and R$^4$ are the same or different and are defined as an aryl group, an arylalkyl group or a straight or branched alkyl group having from 1 to 20 carbon atoms and n is an integer from 1 to 10.

11. The process of claim 10, wherein the aryl, arylalkyl or alkyl groups have from 1 to 10 carbon atoms.

12. The process of claim 11, wherein the alkyl group has from 1 to 4 carbon atoms.

13. The process of claim 10, wherein the arylalkyl group is a benzyl group.

14. The process of claim 10, wherein the polyphosphate ester is hexaethyltetraphosphate.

15. The process of claim 1, wherein the cyanide is soluble in the reaction mixture.

16. The process of claim 1, wherein the cyanide is hydrogen cyanide, an alkali metal cyanide, an alkaline earth metal cyanide, an ammonium cyanide, a tetraalkyl ammonium cyanide, a tetraalkyl phosphonium cyanide, a trialkyl sulfonium cyanide, a cyanide of a cationic form of an organic amine or mixtures thereof.

17. The process of claim 16, wherein the cyanide is hydrogen cyanide, potassium cyanide, sodium cyanide, lithium cyanide, silver cyanide, gold cyanide, copper cyanide, tetrabutylammonium cyanide or mixtures thereof.

18. The process of claim 17, wherein the cyanide is hydrogen cyanide, potassium cyanide, sodium cyanide or tetrabutylammonium cyanide.

19. The process of claim 1, wherein the molar ratio of cyanide ion to phosphate groups added to the reaction mixture is in the range of about 0.9 to about 10.

20. The process of claim 19, wherein the molar ratio of cyanide ion to phosphate groups added to the reaction mixture is in the range of about 1 to about 4.

21. The process of claim 19, wherein the molar ratio of cyanide ion to phosphate groups added to the reaction mixture is in the range of about 0.9 to about 1.2.

22. The process of claim 19, wherein the molar ratio of cyanide ion to phosphate groups added to the reaction mixture is in the range of about 1.5 to about 2.5.

23. The process of claim 1, wherein the temperature of the reaction mixture is in the range of about 0° to about 100° C.

24. The process of claim 23, wherein the temperature of the reaction mixture is in the range of about 20° to about 80° C.

25. The process of claim 24, wherein the temperature of the reaction mixture is in the range of about 30° to about 60° C.

26. The process of claim 1, wherein the reaction mixture further contains a solvent.

27. The process of claim 26, wherein the solvent is a polar aprotic solvent.

28. The process of claim 25, wherein the solvent comprises an amide, a nitrile or an ether.

29. The process of claim 28, wherein the solvent comprises DMF or dimethylacetamide.

30. The process of claim 28, wherein the solvent comprises acetonitrile or propionitrile.

31. The process of claim 28, wherein the solvent comprises tetrahydrofuran or methyl t-butylether.

32. The process of claim 1, wherein the ester is a pyrophosphate ester and the cyanophosphonate derivative produced is a cyanophosphonate monoester monosalt.

33. The process of claim 1, wherein the cyanophosphonate derivative is potassium benzyl cyanophosphonate, potassium methyl cyanophosphonate, potassium ethyl cyanophosphonate, lithium benzyl cyanophosphonate, lithium methyl cyanophosphonate, lithium ethyl cyanophosphonate, sodium benzyl cyanophosphonate, sodium methyl cyanophosphonate or sodium ethyl cyanophosphonate.

34. A process for preparing an aminomethylphosphonate derivative comprising:

contacting a pyrophosphate ester or a polyphosphate ester and a cyanide in a reaction mixture under sufficient conditions to produce a cyanophosphonate derivative, and hydrogenating the cyanophosphonate derivative in the presence of a suitable catalyst under sufficient conditions to produce an aminomethylphosphonate derivative.

35. The process of claim 34, wherein the cyanophosphonate derivative is potassium benzyl cyanophosphonate, potassium methyl cyanophosphonate, potassium ethyl cyanophosphonate, lithium benzyl cyanophosphonate, lithium methyl cyanophosphonate, lithium ethyl cyanophosphonate, sodium benzyl cyanophosphonate, sodium methyl cyanophosphonate or sodium ethyl cyanophosphonate.

36. The process of claim 34, wherein the catalyst comprises a cobalt-containing compound, a nickel-containing compound, a rhodium-containing compound, a platinum-containing compound or a palladium-containing compound.

37. The process of claim 36, wherein the catalyst comprises Raney cobalt, Raney nickel, platinum promoted Raney nickel, platinum on carbon, palladium on carbon or rhodium on carbon.

38. The process of claim 37, wherein the catalyst comprises a Raney nickel catalyst.

39. The process of claim 37, wherein the catalyst is a platinum promoted Raney nickel catalyst.

40. The process of claim 39, wherein the catalyst comprises a platinum tetrachloride ($PtCl_4$) promoted Raney nickel catalyst.

41. The process of claim 37, wherein the catalyst comprises rhodium on carbon, platinum on carbon or palladium on carbon.

42. The method of claim 41, wherein the hydrogenation reaction mixture further contains an acid.

43. The method of claim 42, wherein the acid is an inorganic acid.

44. The method of claim 43, wherein the inorganic acid is hydrochloric acid, sulfuric acid, phosphoric acid, nitric acid or hydrocyanic acid.

45. The method of claim 44, wherein the inorganic acid is hydrochloric acid.

46. The method of claim 42, wherein the acid is an organic acid.

47. The method of claim 46, wherein the organic acid is acetic acid, trifluoroacetic acid, trifluoromethanesulfonic acid or p-toluenesulfonic acid.

* * * * *